United States Patent [19]

Oppawsky

[11] Patent Number: 4,839,521
[45] Date of Patent: Jun. 13, 1989

[54] TREATMENT CHAMBER FOR THE PHOTOPOLYMERIZATION OF DENTAL PLASTICS

[75] Inventor: Steffen Oppawsky, Bad Homburg, Fed. Rep. of Germany

[73] Assignee: Kulzer & Co. GmbH, Wehrheim, Fed. Rep. of Germany

[21] Appl. No.: 157,929

[22] Filed: Feb. 19, 1988

[30] Foreign Application Priority Data

Mar. 13, 1987 [DE] Fed. Rep. of Germany ....... 3708204

[51] Int. Cl.[4] .............................................. G21K 5/08
[52] U.S. Cl. .............................. 250/453.1; 250/455.1; 250/492.1; 250/504 R; 250/504 H
[58] Field of Search ............... 250/453.1, 455.1, 492.1, 250/504 R, 504 H; 350/1.7

[56] References Cited

U.S. PATENT DOCUMENTS

| | | | |
|---|---|---|---|
| 3,398,040 | 8/1968 | Allen et al. | 350/1.7 |
| 3,488,495 | 1/1970 | Schneeman | 250/453.1 |
| 3,519,517 | 7/1970 | Dench | 156/380 |
| 4,412,134 | 10/1983 | Herold et al. | 250/455.1 |

FOREIGN PATENT DOCUMENTS 2098439 11/1982 United Kingdom .

Primary Examiner—Bruce C. Anderson
Assistant Examiner—Jack I. Berman
Attorney, Agent, or Firm—Felfe & Lynch

[57] ABSTRACT

A treatment chamber as an accessory device for an illuminator for the photopolymerization of dental plastics. The chamber is both light-tight and has at least one movable chamber wall. A light conductor is provided for the light input.

14 Claims, 4 Drawing Sheets

TREATMENT CHAMBER FOR THE PHOTOPOLYMERIZATION OF DENTAL PLASTICS

FIELD OF THE INVENTION

The invention relates to a treatment chamber used as an accessory device for an illuminator for the photopolymerization of dental plastics such as methacrylic resins. In particular, the chamber has interior walls which are light reflective, an opening on one wall to transmit light into the interior of the chamber, a light trap and a terminal for a light conductor.

BACKGROUND OF THE INVENTION

A treatment chamber is disclosed in GB patent No. 1,485,908 which is used for the heating of solder by radiation produced in an illuminator and delivered by means of a light conductor to the interior of the treatment chamber. The treatment chamber is provided with a loading slot for the insertion of the material to be treated into the interior of the chamber. The device is not useful as a treatment chamber for photopolymerization of dental plastics because some light will emit through the loading slot. This will result in an unsymmetrical irradiation of the dental plastics and cause incomplete curing or hardening of the plastics.

It is the object of this invention to construct a treatment chamber that is universally usable in the field of dental technology in which materials are treated with light, especially useful for the treatment by photopolymerization of articles made from dental plastics.

SUMMARY OF THE INVENTION

This object is achieved by the inventive treatment chamber having light reflective interior walls which is light-tight or impenetrable to exterior light, and by having at least one of the walls defining the chamber as a sliding wall or a hinged wall.

The inventive treatment chamber has the advantage that no harmful light can reach the eyes of the operator. This is especially important when dental plastics are photopolymerized in the treatment chamber using light in the short-wavelength visible range of the spectrum (i.e. 400–500 nanometers) and/or from the ultraviolet spectral range (i.e. 320–400 microns). At the same time, however, the interior of the chamber remains easily accessible for loading with the material to be treated.

In a first preferred embodiment of the treatment chamber, the wall forming the floor of the chamber and the wall containing the opening for the input of light are stationary with respect to the other walls.

In a second preferred embodiment of the treatment chamber the chamber floor is movable with respect to the wall containing the opening for the input of light.

To assure that the chamber will not leak light to the outside, it has been found advantageous in all embodiments of these treatment chambers to provide the edges of the fixed walls with a light trap to be engaged by the edges of the movable walls. The light trap is advantageously in the form of grooves, in the form of at least one rib, or in the form of sealing flanges. A filter is also preferably used to reflect or absorb light having a wavelength which is longer than 500 nanometers.

The light input or "light" used for the photopolymerization of dental plastics is preferably in the light spectral range of from 350–500 microns and is provided to the treatment chamber by means of a light conductor, which can be in the form, for example, of a liquid light conductor, a fiber light conductor or a quartz glass rod. The light conductor is attached to the treatment chamber at the opening by means of a light conductor socket which is disposed on the outside of the chamber wall containing the opening for the input of light. One end of the light conductor extends into the light conductor socket at a point close to the opening in the chamber wall. The other, free end of the light conductor is inserted into the terminal provided in the illuminator when the treatment chamber is in the operating state.

Between the end of the light conductor disposed in the light conductor socket and the opening in the chamber wall at least one light filter or diaphragm may be introduced into the beam path. In the preferred embodiment a slide is provided to extend through the light conductor socket and carry the filter. By means of light filters of different spectral admittance it is possible to adapt the light to different thermal and spectral sensitivities of the dental plastics to be photopolymerized.

Also, the slide can be used for blocking the entrance of light into the treatment chamber, especially when material to be treated is introduced into the treatment chamber or treated material is removed therefrom, without the necessity of shutting off the light source in the illuminator or drawing the light conductor out of the socket provided on the illuminator.

Preferably, a viewing window can be inserted in either a side wall of the chamber or in the chamber top, and the viewing window may be provided with a light-reflective coating on its surface facing the chamber interior. This coating may be, for example, a vapor-deposited interference mirror which reflects the short-wavelength part of the radiation (e.g. shorter than 400 nanometers) used to photopolymerize the dental plastics, such as methacrylic resins, but transmits the longer-wavelength radiation in the visible range (e.g. 400–500 nanometers). It is thus possible to observe the material during its treatment.

The objects discussed in the foregoing and additional objects which will be apparent to those skilled in the art are achieved by the inventive accessory for an illuminator used to harden plastic dental filling used in the mouth. The accessory may also be in the form of a hand unit which can easily be coupled to such an illuminator and permits a great number of dental technology operations without the procurement of a complex apparatus.

DETAILED DESCRIPTION OF THE PREFERRED EMBODIMENTS

Figure 1:
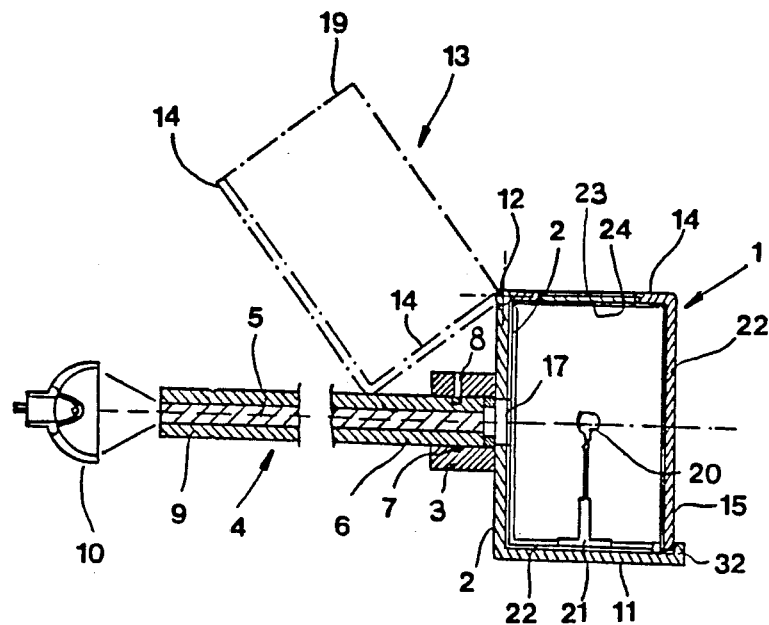
FIG. 1 is a vertical cross section through an embodiment of the accessory device having a hinged hood.

The accessory device shown in FIG. 1 has a chamber on whose wall 2 a socket 3 for a light conductor 4 is disposed. The light conductor 4 consists of a fiber core 5 which is surrounded by a stiffening sleeve 6, preferably of aluminum. The stiffening sleeve 6 is preferably provided on one end facing the chamber 1 with an annular groove 7 which is engaged by a spring element 8 or an adjusting screw of the socket 3, so that he stiffening sleeve 6 is locked in the socket 3. Any other suitable engaging means known in the art may be employed.

The other end 9 of the light conductor facing away from the chamber 1 may be connected to an illuminator for the photopolymerization of dental plastics, whose radiation source 10 may be in the form of a lamp with a reflector as indicated in FIG. 1.

The accessory device is preferably a cantilevered unit, so that the stiffening sleeve 6 not only protects the fiber core 5 but serves at the same time as an arm to support the chamber 1. If desired, feet (not shown) may be disposed on the bottom 11 of the chamber 1 on which the chamber to stand the chamber 1 on a work platform.

The chamber 1 has a hood 13 which hinges about a horizontal axis 12 formed by the chamber roof 14 and the wall 15 which is situated opposite the back wall 2 having the opening 17 through which light from the light conductor 4 is emitted into the chamber 1. The hinge axis 12 of the hood 13 runs along the upper edge of the back wall 2. The side walls 18 directly adjoining the back wall 2 can either be fixedly joined to the back wall 2 and the bottom 11 of the chamber 1 or, as indicated in phantom lines 19 in FIG. 1, be hinged to the back wall 2 to form side walls of the hood 13. The hinged embodiment (i.e. shown in phantom lines) offers the advantage that the area in front of the opening 17 for the input of light is freely accessible for loading the chamber 1 with a plastic part 20 to be irradiated. The part 20 is preferably held on a holder or support 21.

All of the chamber walls 2, 15 and 18 as well as the bottom 11 and the roof 14 of the chamber are preferably clad with a light-reflecting material 22 to form a reflector. If the chamber walls are made of a metal material, they preferably have a polished inside surface so that the entire interior of the chamber forms a reflector. It may be appreciated that at least the chamber roof 14 and the wall 15 opposite the opening 17 may bulge in a convex shape in order to focus the radiation at the approximate center of the chamber 1 in which the plastic part is positioned.

Figure 2:
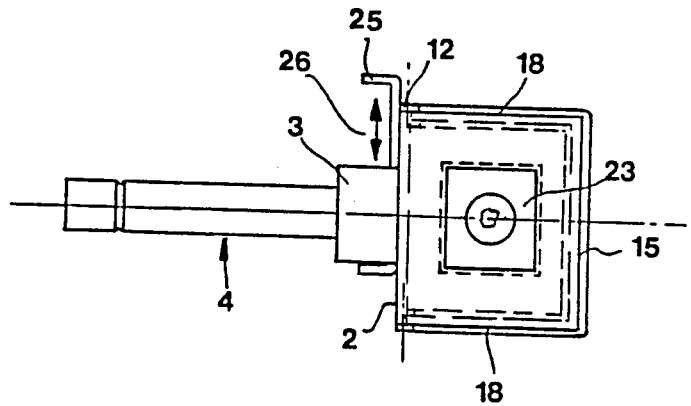
FIG. 2 is a top plan view of the accessory device illustrated in FIG. 1.

As shown especially in FIG. 2, a viewing window 23 is inserted into the chamber roof 14, and has on its interior surface facing the interior of the chamber a reflective covering 24. This reflective covering 24 can be, for example, a mirrored material which on the one hand reflects the radiation in the interior of the chamber 1, and on the other hand is transparent from the outside of the chamber 1, so that an operator may check the plastic part 20 for correct positioning during operation of the device.

A slide 25 may also be provided between the socket 3 of the light conductor 4 and the back wall 2, as shown in FIG. 2. Such a slide may have a diaphragm, not shown, or one or more filters inserted into it, and is preferably displaced in the direction of the arrow 26 in order to position the filter or the diaphragm in front of the opening 17 in the wall 2.

Figure 3:
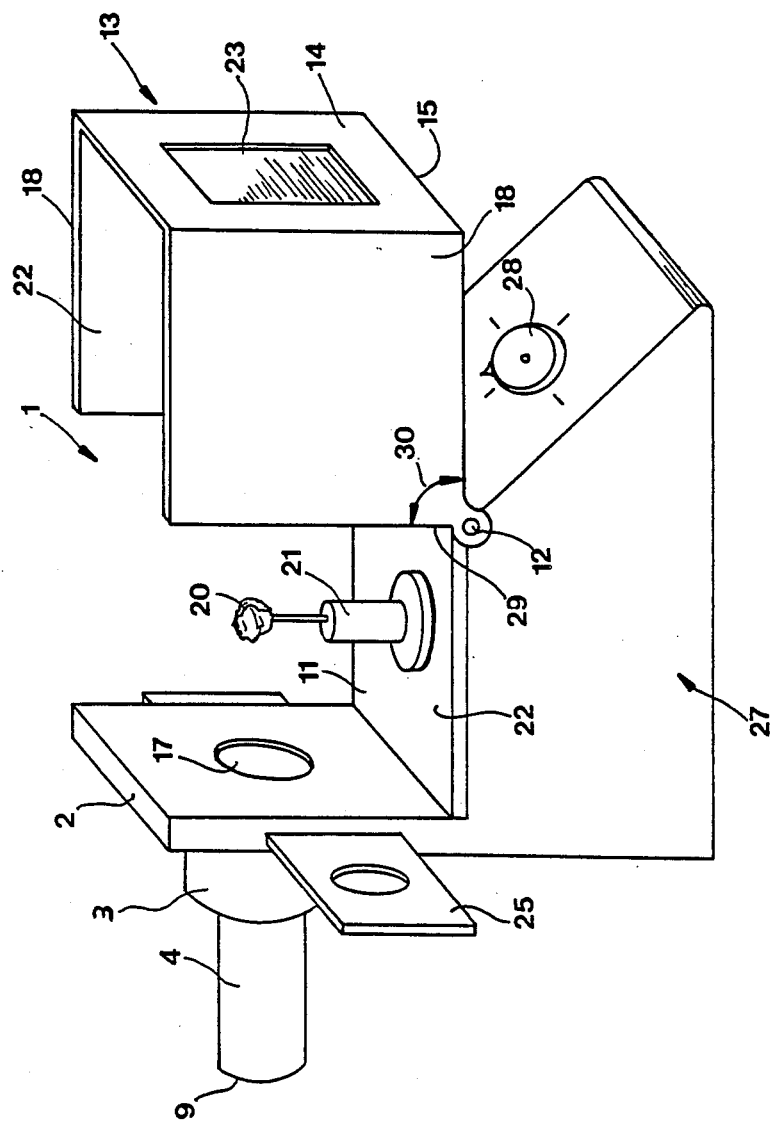
FIG. 3 is a perspective view of a free-standing accessory device having a hinged hood.

While the accessory device illustrated in FIGS. 1 and 2 is a cantilevered unit, the accessory device may also be built as a free-standing unit, such as the units illustrated in FIGS. 3 an 4.

The free-standing units have a housing 27 on top of which the chamber 1 is placed. The floor 11 of the chamber 1 may simultaneously form the roof of the housing 27. Feet (not shown) may be provided. On the bottom of the housing 27, which may be backed out of the bottom plate so as to set the hood 13 at different heights above a work table, so that the position of the socket 3 of the light conductor 4 can be adjusted to the position of the socket of an illuminator. In this free-standing unit a timing relay is inserted into the housing 27, with an operating dial 28 on the rely front, by which the irradiation time can be set. In a preferred embodiment, a receptacle for the power supply of the illuminator is disposed on the back of the housing 27, so that the delivery of power to the illuminator will be interrupted by the timing relay at the end of the required irradiation time.

In contrast to the embodiment according to FIG. 1 and FIG. 2, the hood 13 as illustrated in FIG. 3 is preferably held on an articulation on the front edge 29 of the floor 11, indicated by the axis of rotation 12 in the direction of the arrow 30. In the open position the hood 13 lies against an abutment so that the opening angle will be limited to the position of the hood 13 shown in FIG. 3. The hood in this case is made up of the chamber roof 14 with the viewing window 23, the two lateral walls 18, and the front wall 15. In the opening position the interior of the chamber is freely accessible from three sides.

Figure 4:
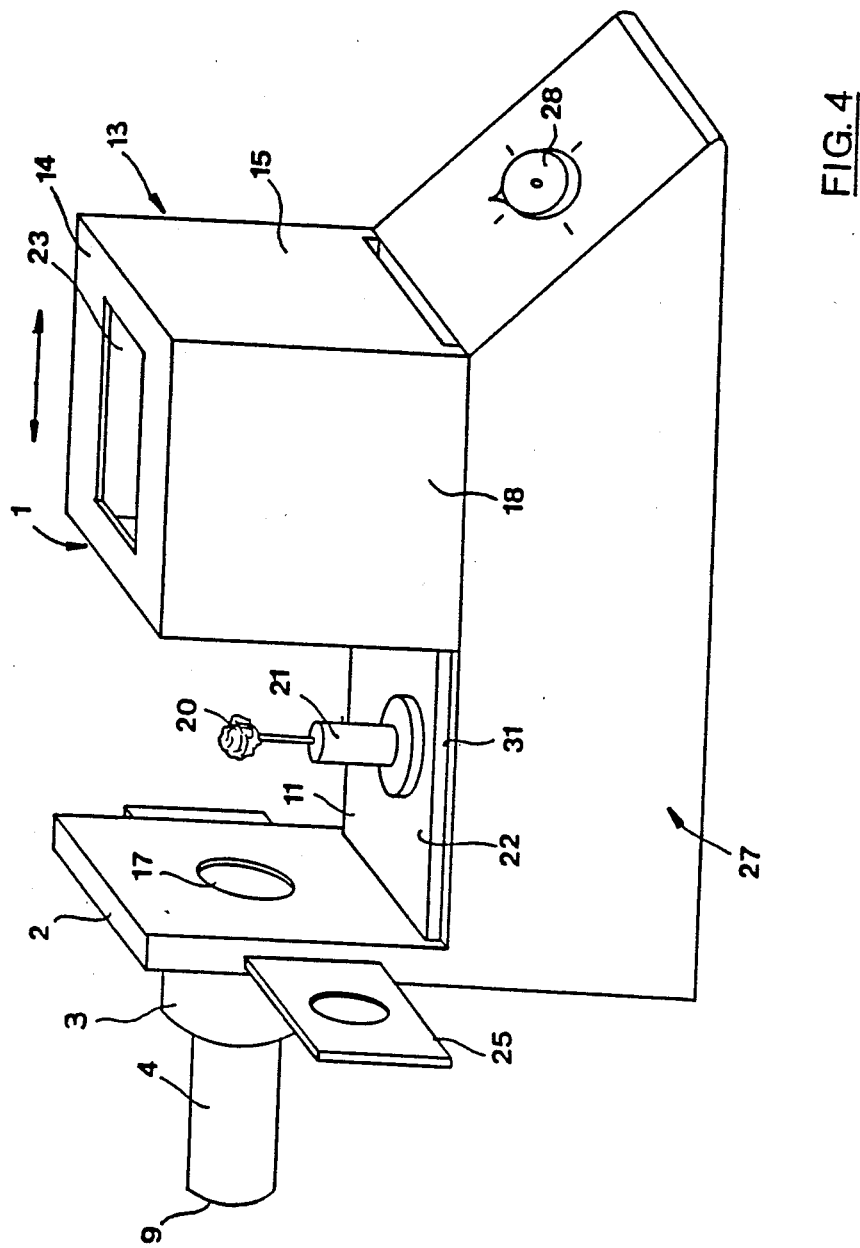
FIG. 4 is a perspective view of a second embodiment of the free-standing accessory device of FIG. 3 having a hood displaceably guided on rails.

In another preferred embodiment, the hood 13 of the chamber 1 may be disposed so as to slide on tracks 31 on the housing 27 to thus open and close the chamber, as illustrated in FIG. 4. A good guidance of the hood 13 is assured by the fact that the housing 27 is made longer than the embodiment according to FIG. 3, so that when the hood is open it lies on the tracks 31.

Figure 5:
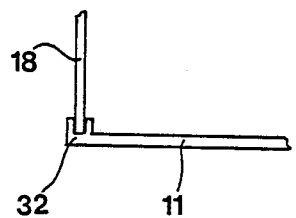
FIG. 5 is a vertical cross section view illustrating a light trap.
Figure 6:
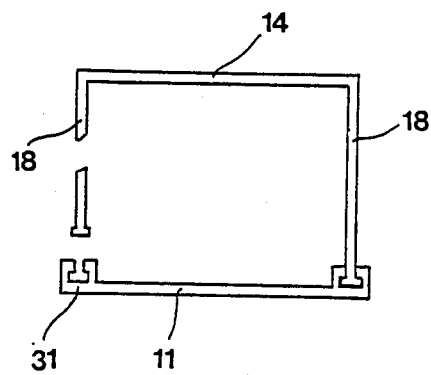
FIG. 6 is a top view schematically illustrating a hood guided in rails on the bottom plate.

The tracks 31 which cradle the edge of the hood 13 or wrap around it (see FIG. 6) form at the same time a light trap which assures that no light harmful to the eyes of the operator will reach the exterior from the inside of the chamber. In order to seal all of the edge of the hood against the escape of light, sealing flanges or ribs 32 are associated with those edges of the hood 13 which are not guided by a track 31, as indicated at the front edge of the floor 11 in FIG. 1 and represented in FIG. 5. These sealing flanges or ribs 32 are situated preferably on the walls of chamber 1 which belong to the hood 13 which are not hinged.

It will be understood that the specification is illustrative but not limitative of the present invention in that other embodiments within the spirit and scope of the invention will suggest themselves to those skilled in the art.

I claim:

1. An accessory device for photopolymerization of a dental plastic by a light input from an illuminator comprising:

a light-tight chamber having walls with interior surfaces which are light reflective to reflect the light of the light input from the walls, one of said walls defining an opening to permit the light input from the illuminator into the chamber;

a closure means attached to at least one of said walls for displaceably opening the chamber and providing access to the dental plastic in the chamber; and a light conductor socket affixed to an exterior surface of the wall of the chamber defining the opening, the socket positioned between the chamber and the illuminator at the level of the opening such that the light input from the illuminator travels through the light conductor socket and the opening into the chamber.

2. The accessory device according to claim 1, wherein the closure means comprises:

a hinge means affixed to one of said walls of the chamber and extending in a parallel direction relative to a horizontal axis of the chamber for displaceably opening the chamber.

3. The accessory device according to claim 1, wherein the closure means comprises:

a sliding means attached to at least one of said walls of the chamber for reversibly sliding the walls of the chamber to provide access to the dental plastic.

4. The accessory device according to claim 2, wherein the walls of the chamber comprise:

a chamber floor adjacent to the wall defining the opening for the light input, the chamber floor and the wall defining the opening being stationary relative to the other walls of the chamber.

5. The accessory device according to claim 3, wherein the walls of the chamber comprise:

a chamber floor being movable relative to the wall defining the opening for the light input.

6. The accessory device according to claim 1, wherein the walls of the light-tight chamber further comprise:

a light trap means engaging an exterior corner of the chamber for preventing light from an exterior of the chamber from entering the chamber.

7. The accessory device according to claim 6, wherein the light trap means comprises:

a groove extending in the chamber floor and accommodating at least one of the walls of the chamber; and a sealing flange positioned at one end of the groove on the chamber floor to seal close the chamber from light from the exterior.

8. The accessory device according to claim 1 wherein the light conductor socket further comprises a slide means for containing a light filter at the level of the opening.

9. The accessory device according to claim 8 wherein the slide means further comprises a diaphragm.

10. The accessory device according to claim 1 wherein at least three of the walls of the chamber, including the wall defining the opening for the light input, define a hood of the chamber.

11. The accessory device according to claim 10 wherein the hood is hinged about an articulation mounting on the wall defining the opening for displaceably opening the chamber and providing access to the dental plastic.

12. The accessory device according to claim 11 wherein the articulation is disposed on an upper edge of the wall defining the opening and has a hinge axis extending parallel to a horizontal axis of the chamber.

13. The accessory device according to claim 10 wherein the hood comprises a guiding track positioned on a floor of the chamber to reversibly slide the hood from an open to a closed position to provide access to the dental plastic in the chamber.

14. The accessory device according to claim 1 wherein a viewing window is provided in one of the walls of the chamber, the viewing window having a reflective coating on an interior surface of the window facing the chamber for reflecting the light input in the chamber.

* * * * *